United States Patent
Zabrouskov et al.

(10) Patent No.: US 10,067,141 B2
(45) Date of Patent: Sep. 4, 2018

(54) SYSTEMS AND METHODS FOR IMPROVING LOADING CAPACITY OF A SEGMENTED REACTION CELL BY UTILIZING ALL AVAILABLE SEGMENTS

(71) Applicant: Thermo Finnigan LLC, San Jose, CA (US)

(72) Inventors: Vladimir Zabrouskov, Belmont, CA (US); Christopher Mullen, Menlo Park, CA (US)

(73) Assignee: Thermo Finnigan LLC, San Jose, CA (US)

( * ) Notice: Subject to any disclaimer, the term of this patent is extended or adjusted under 35 U.S.C. 154(b) by 101 days.

(21) Appl. No.: 15/188,858

(22) Filed: Jun. 21, 2016

(65) Prior Publication Data
US 2017/0363638 A1    Dec. 21, 2017

(51) Int. Cl.
*G01N 33/68*    (2006.01)
*H01J 49/00*    (2006.01)
*H01J 49/42*    (2006.01)

(52) U.S. Cl.
CPC ...... *G01N 33/6851* (2013.01); *H01J 49/0031* (2013.01); *H01J 49/0072* (2013.01); *H01J 49/422* (2013.01)

(58) Field of Classification Search
CPC .. H01J 49/0031; H01J 49/0072; H01J 49/422; G01N 33/6851
See application file for complete search history.

(56) References Cited

U.S. PATENT DOCUMENTS

| | | | |
|---|---|---|---|
| 7,534,622 B2 * | 5/2009 | Hunt | G01N 33/6848 436/173 |
| 2004/0135080 A1 | 7/2004 | Ouyang et al. | |
| 2005/0199804 A1 | 9/2005 | Hunt et al. | |
| 2009/0032700 A1 | 2/2009 | Park et al. | |
| 2010/0108880 A1 | 5/2010 | Stoermer | |
| 2011/0284741 A1 | 11/2011 | Stoermer et al. | |
| 2015/0287585 A1 | 10/2015 | Kovtoun et al. | |

FOREIGN PATENT DOCUMENTS

| | | |
|---|---|---|
| EP | 2388798 A1 | 11/2011 |
| WO | 2005/074004 A2 | 8/2005 |
| WO | 2008/000083 A1 | 1/2008 |
| WO | 2008/008634 A2 | 1/2008 |
| WO | 2009/147411 A2 | 12/2009 |
| WO | 2010/002819 A1 | 1/2010 |
| WO | 2011/092515 A1 | 8/2011 |
| WO | 2011/095465 A2 | 8/2011 |
| WO | 2015/097503 A1 | 7/2015 |

* cited by examiner

*Primary Examiner* — Christopher Hixson
(74) *Attorney, Agent, or Firm* — David Schell (57) ABSTRACT

A method for analyzing a sample includes trapping a first ion packet in a first segment of a multi-segment reaction cell; trapping a second ion packet in a second segment of the multi-segment reaction cell; and trapping a third ion packet in a third segment of the multi-segment reaction cell. At least one of the first, second, and third ion packets includes precursor ions, and at least another one of the first, second, and third ion packets includes reagent ions. The method further includes mixing the first, second, and third ion packets within the reaction cell to cause a reaction between the precursor ions and the reagent ions to form product ions.

23 Claims, 7 Drawing Sheets

SYSTEMS AND METHODS FOR IMPROVING LOADING CAPACITY OF A SEGMENTED REACTION CELL BY UTILIZING ALL AVAILABLE SEGMENTS

FIELD

The present disclosure generally relates to the field of mass spectrometry including systems and methods for improving loading capacity of a segmented reaction cell by utilizing all available segments.

Introduction

Gas-phase ion/ion reactions has proven to be a flexible means for probing and manipulating analyte ions with particular utility in bioanalysis. For example, reactions between an analyte ion and a reactant ion to fragment the analyte ion can provide structural information through the observation of fragment mass to charge ratio and fragmentation patterns. Various techniques for ion-ion reactions are known in the art, such as electron transfer dissociation (ETD), negative electron transfer dissociation (nETD), proton transfer reaction (PTR).

ETD and nETD are methods of fragmenting ions in a mass spectrometer. Similar to electron-capture dissociation, ETD induces fragmentation of a precursor cation by transferring electrons from a reactant. Rather than utilizing free electrons, ETD uses radiacal anions, such as anthracene, fluoranthene, or azobenzene. Similarly, nETD induces fragmentation by transferring electrons from a precursor anion to a radical cation reactant. ETD and nETD can work well for higher charge state ions (z>2), however relative to collision-induced dissociation (CID), ETD is advantageous for the fragmentation of longer peptides or even entire proteins.

ETD can be useful for the identification of peptides or proteins. ETD cleaves randomly along the peptide backbone. This produces primarily c- and z-type fragment ions that complement the b- and y-type ions produced by CID, increasing sequence coverage and protein identification. While ETD cleaves the peptide backbone, side chains and modifications such as phosphorylation are left intact making ETD especially useful for identifying modification sites. This makes the technique important for top-down proteomics.

Precursor species and reagent species of opposite polarity can be reacted by holding both the cations and the anions in an ion trap or other device. As with any chemical reaction, the kinetics depend on the concentrations of the cations and anions. Furthermore, the degree of fragmentation depends on the relative abundance of the cations and anions as well as the length of time spent within the reaction vessel. Thus, to achieve a desired degree of fragmentation of the precursors, it is advantageous to control the amount of precursor, amount of reactant, and the length time the reagent ions can react with precursor ions and the resulting fragment ions.

From the foregoing it will be appreciated that a need exists for improved systems and methods for loading precursor ions and reactant ions in an multi-segmented reaction cell.

SUMMARY

In a first aspect, a method for analyzing a sample can include trapping a first ion packet in a first segment of a multi-segment reaction cell; trapping a second ion packet in a second segment of the multi-segment reaction cell; and trapping a third ion packet in a third segment of the multi-segment reaction cell. At least one of the first, second, and third ion packets includes precursor ions, and at least another one of the first, second, and third ion packets includes reagent ions. The method can further include mixing the first, second, and third ion packets within the reaction cell to cause a reaction between the precursor ions and the reagent ions to form product ions.

In various embodiments of the first aspect, the multi-segment reaction cell is a segmented linear ion trap, a higher-energy dissociation (HCD) cell, a multipurpose dissociation cell, or any combination thereof.

In various embodiments of the first aspect, the method can further include supplying a sample to an ion source and generating the precursor ions.

In various embodiments of the first aspect, the method can further include supplying a reagent to an ion source and generating the reagent ions.

In various embodiments of the first aspect, the method can further include directing the product ions to a mass analyzer to determine the mass-to-charge ratio of the product ions. In particular embodiments, the method can further include identifying a component of the sample based on the mass-to-charge ratio of the product ions.

In various embodiments of the first aspect, the first and third segments can be outer segments of the multi-segment reaction cell and the second segment can be a center segment of the multi-segment reaction cell.

In various embodiments of the first aspect, the first and third ion packets can include reagent ions and the second ion packet can include precursor ions.

In various embodiments of the first aspect, the first and third ion packets can include precursor ions and the second ion packet can include reagent ions.

In various embodiments of the first aspect, the precursor ions can include a mixture of more than one precursor ion species. In particular embodiments, the more than one precursor ion species can be in separate ion packets. In particular embodiments, the more than one precursor ion species can be in the same ion packet.

In various embodiments of the first aspect, the reagent ions can include a mixture of more than one reagent ion species. In particular embodiments, the more than one reagent ion species can be in separate ion packets. In particular embodiments, the more than one reagent ion species can be in the same ion packet.

In various embodiments of the first aspect, the method can further include trapping additional ion packets in additional segments of the multi-segment reaction cell prior to mixing the ion packets.

In a second aspect, a system for analyzing a sample can include a multi-segment reaction cell including at least first, second, and third segments; a sample ion source configured to receive a sample and generate precursor ions; a mass analyzer configured to determine the mass-to-charge ratio of product ions; and a controller. The controller can be configured to instruct the trapping of a first ion packet in a first segment of the multi-segment reaction cell, instruct the trapping of a second ion packet in a second segment of the multi-segment reaction cell, instruct the trapping of a third ion packet in a third segment of the multi-segment reaction cell, wherein at least one of the first, second, and third ion packets includes precursor ions, and at least another one of the first, second, and third ion packets includes reagent ions; and instruct the mixing of the first, second, and third ion packets within the reaction cell to cause a reaction between the precursor ions and the reagent ions to form product ions.

In various embodiments of the second aspect, the system can further include a reagent ion source configured to receive a reagent and generate reagent ions.

In various embodiments of the second aspect, the sample ion source can be further configured to receive a reagent and generate reagent ions.

In various embodiments of the second aspect, the system can further include a processor configured to identifying a component of the sample based on the mass-to-charge ratio of the product ions.

In various embodiments of the second aspect, the first and third segments can be outer segments of the multi-segment reaction cell and the second segment can be a center segment of the multi-segment reaction cell.

In various embodiments of the second aspect, the first and third ion packets can include reagent ions and the second ion packet can include precursor ions.

In various embodiments of the second aspect, the first and third ion packets can include precursor ions and the second ion packet can include reagent ions.

In various embodiments of the second aspect, the precursor ions can include a mixture of more than one precursor ion species. In particular embodiments, the more than one precursor ion species can be in separate ion packets. In particular embodiments, the more than one precursor ion species can be in the same ion packet.

In various embodiments of the second aspect, the reagent ions include a mixture of more than one reagent ion species. In particular embodiments, the more than one reagent ion species can be in separate ion packets. In particular embodiments, the more than one reagent ion species can be in the same ion packet.

In various embodiments of the second aspect, the multi-segment reaction cell includes additional segments and the controller is further configured to instruct the trapping of additional ion packets in the additional segments of the multi-segment reaction cell prior to mixing the ion packets.

In various embodiments of the second aspect, the multi-segment reaction cell is a segmented linear ion trap, a higher-energy dissociation (HCD) cell, a multipurpose dissociation cell, or any combination thereof.

DRAWINGS

For a more complete understanding of the principles disclosed herein, and the advantages thereof, reference is now made to the following descriptions taken in conjunction with the accompanying drawings, in which.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for ion separation are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.
Mass Spectrometry Platforms Various embodiments of mass spectrometry platform 100 can include components as displayed in the block diagram of FIG. 1. In various embodiments, elements of FIG. 1 can be incorporated into mass spectrometry platform 100. According to various embodiments, mass spectrometer 100 can include an ion source 102, a mass analyzer 104, an ion detector 106, and a controller 108. Optionally, the mass spectrometry platform 100 can further include a second ion source 110.

Figure 1:
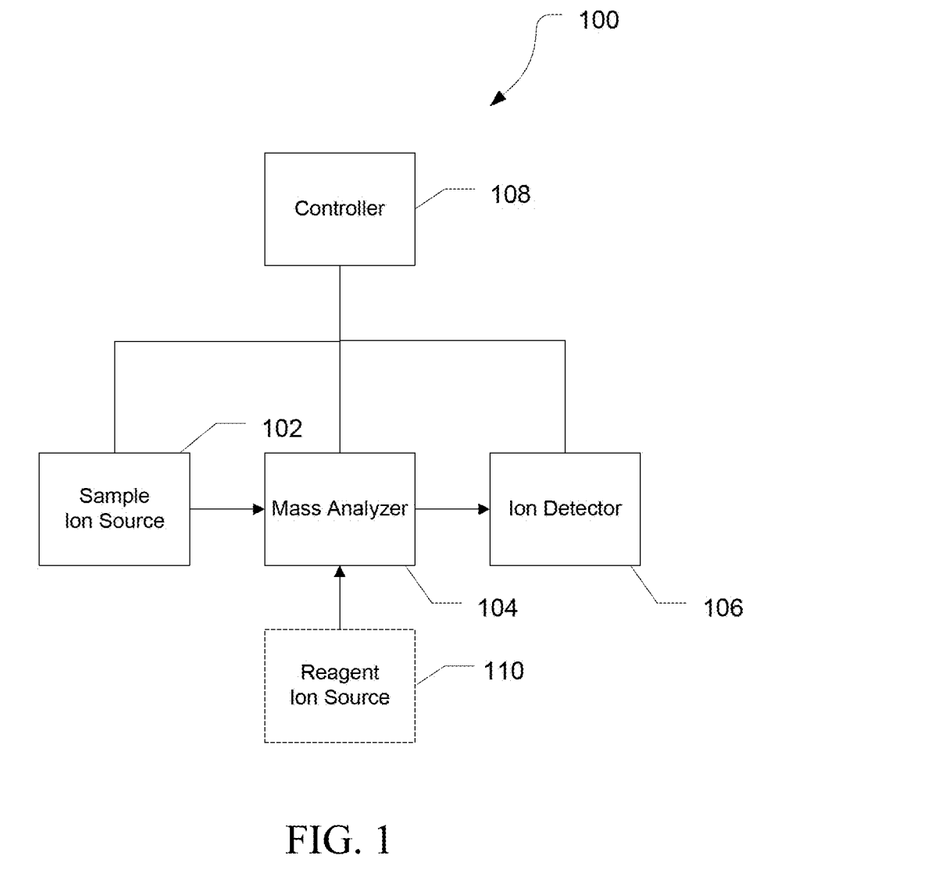
FIG. 1 is a block diagram of an exemplary mass spectrometry system, in accordance with various embodiments.

In various embodiments, the ion source 102 generates a plurality of ions from a sample. The ion source can include, but is not limited to, a matrix assisted laser desorption/ionization (MALDI) source, electrospray ionization (ESI) source, atmospheric pressure chemical ionization (APCI)

source, atmospheric pressure photoionization source (APPI), inductively coupled plasma (ICP) source, electron ionization source, chemical ionization source, photoionization source, glow discharge ionization source, thermospray ionization source, and the like. Similarly, optional second ion source 110 can generate reagent ions from a reagent source. Alternatively, ion source 102 can be used to generate both sample ions and reagent ions.

In various embodiments, the mass analyzer 104 can separate ions based on a mass-to-charge ratio of the ions. For example, the mass analyzer 104 can include a quadrupole mass filter analyzer, a quadrupole ion trap analyzer, a time-of-flight (TOF) analyzer, an electrostatic trap mass analyzer (e.g., ORBITRAP mass analyzer), Fourier transform ion cyclotron resonance (FT-ICR) mass analyzer, and the like. In various embodiments, the mass analyzer 104 can also be configured to fragment the ions using collision induced dissociation (CID), electron transfer dissociation (ETD), negative electron transfer dissociation (nETD), proton transfer reaction (PTR), electron capture dissociation (ECD), photo induced dissociation (PID), surface induced dissociation (SID), and the like, and further separate the fragmented ions based on the mass-to-charge ratio.

In various embodiments, the ion detector 106 can detect ions. For example, the ion detector 106 can include an electron multiplier, a Faraday cup, and the like. Ions within or leaving the mass analyzer can be detected by the ion detector. In various embodiments, the ion detector can be quantitative, such that an accurate count of the ions can be determined.

In various embodiments, the system can include ion optics to guide and focus ions as they move from the ion source 102 to the mass analyzer 104. Additional ion optics may be utilized to guide or focus ions as they move from the mass analyzer 104 to the ion detector 106. The ion optics can include ion lenses, ion guides, and the like.

In various embodiments, the controller 108 can communicate with the ion source 102, the mass analyzer 104, and the ion detector 106. For example, the controller 108 can configure the ion source or enable/disable the ion source. Additionally, the controller 108 can configure the mass analyzer 104 to select a particular mass range to detect. Further, the controller 108 can adjust the sensitivity of the ion detector 106, such as by adjusting the gain. Additionally, the controller 108 can adjust the polarity of the ion detector 106 based on the polarity of the ions being detected. For example, the ion detector 106 can be configured to detect positive ions or be configured to detected negative ions.

Segmented Reaction Cell Loading

Figure 2:
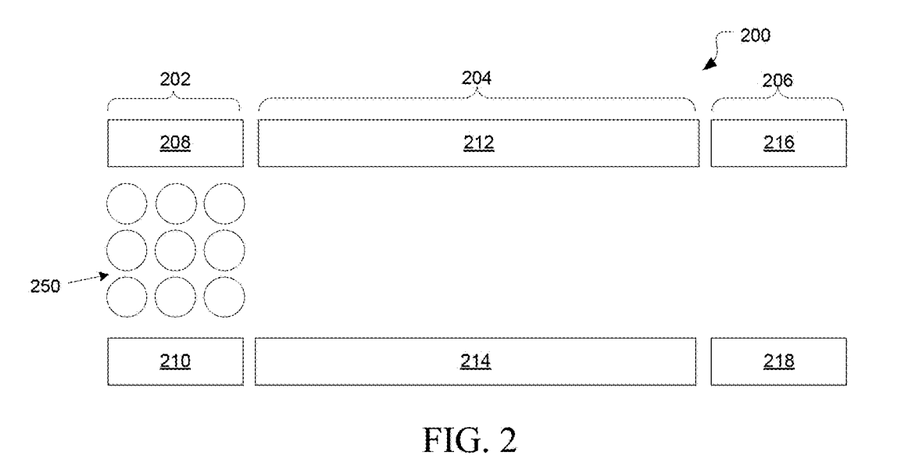
FIGS. 2, 3, 4, 5, and 6 are diagram of an exemplary loadings of a segmented reaction cell, in accordance with various embodiments.
Figure 3:
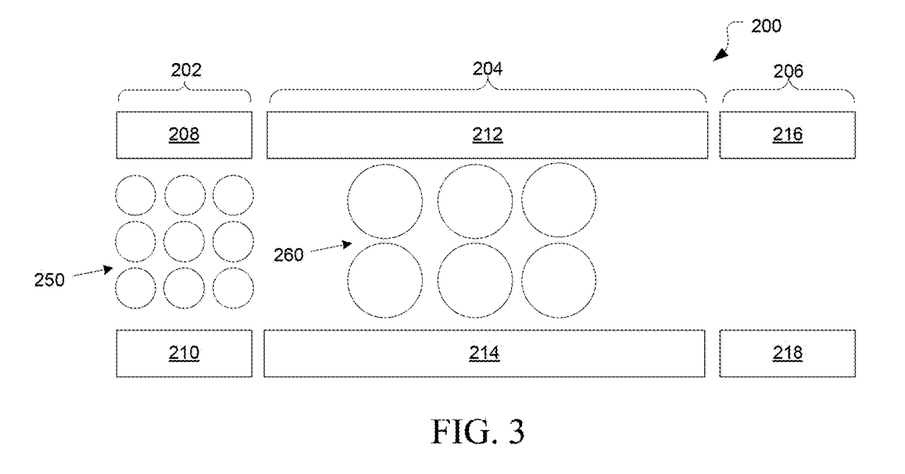
Figure 4:
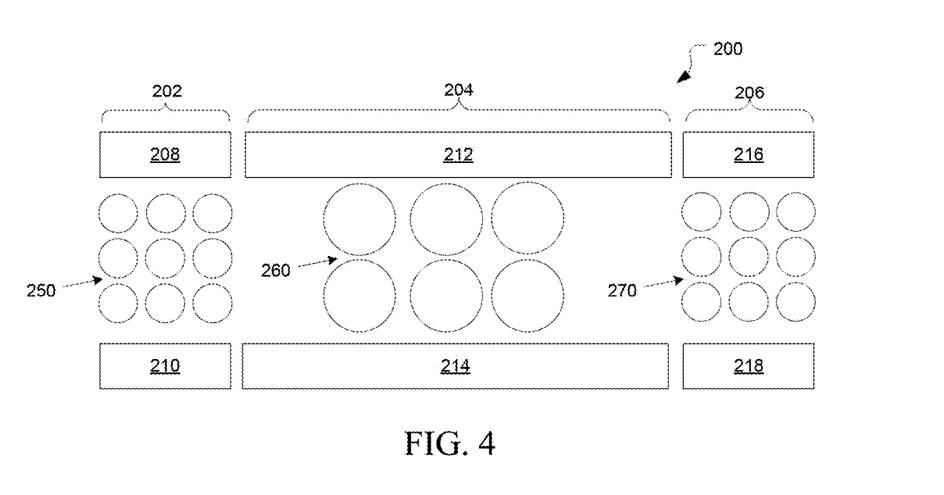

FIGS. 2, 3, and 4 illustrate loading precursor ions and reagent ions into a segmented reaction cell, such as a linear ion trap. The reaction cell on trap 200 consists of 3 segments 202, 204, and 206. The segments include a plurality of rods, such as rods 208 and 210 in segment 202, rods 212 and 214 in segment 204, and rods 216 and 218 in segment 206. In various embodiments, each segment can include 4 rods, although alternative arrangements with more rods per segment are possible. FIGS. 2, 3 and 4 show a cross section so not all rods are visible. Ions can be held within the trap by RF fields generated by applying an RF potential to the rods. Generally, opposing RF potentials (180° out of phase) are applied to neighboring rods within the segment.

In FIG. 2, a packet of ions 250 is loaded into segment 202. In FIG. 3, a packet of ions 260 has been loaded into segment 204 while a packet of ions 250 remains in segment 202. In FIG. 4, a packet of ions 270 has been loaded into segment 206 while packet of ions 250 remain in segment 202 and packet of ions 260 remain in segment 204.

In various embodiments, ion packets 250 and 270 can include precursor ions and ion packet 260 can include reagent ions. When ion packets 250 and 270 include the same species of precursor ion, the number of precursor ions in the trap can be effectively doubled. Alternatively, when ion packet 250 includes a different ion species than ion packet 270, two precursor ion species can be reacted with the reagent ions in ion packet 260 substantially simultaneously.

In various embodiments, ion packets 250 and 270 can include reagent ions and ion packet 260 can include precursor ions. When ion packets 250 and 270 include the same species of reagent ion, the number of reagent ions in the trap can be effectively doubled. Alternatively, when ion packet 250 includes a different ion species than ion packet 270, two reagent ion species can be reacted with the precursor ions in ion packet 260 substantially simultaneously.

Figure 5:
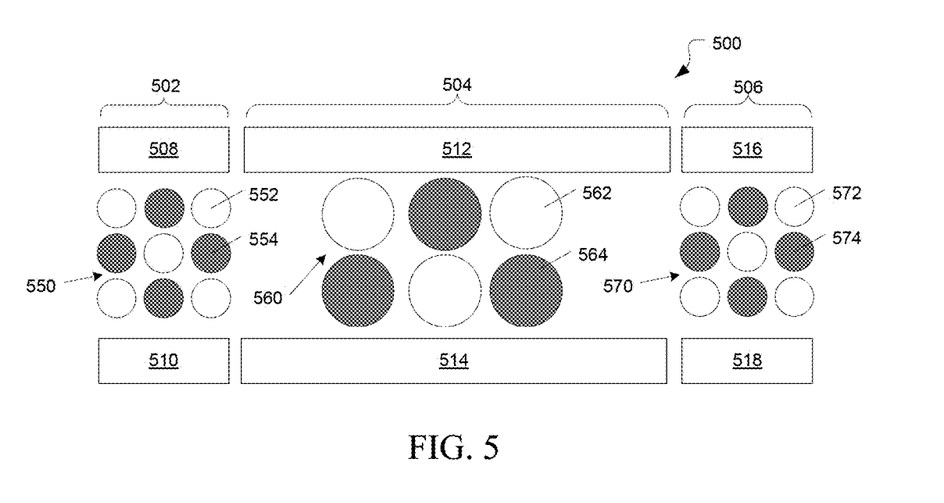

FIG. 5 illustrates a segmented ion trap 500 similar to segmented ion trap 200. As with ion trap 200, ion trap 500 includes segments 502, 504, and 506 and the segments include rods 508 and 510, rods 512 and 514, and rods 516 and 518 respectively. As shown, ion trap 500 is loaded with ion packet 550 in segment 502, ion packet 560 in segment 504, and ion packet 570 in segment 506. However, the ion packets can be multiplexed to contain more than one species of ion. Ion packet 550 includes ion species 552 and ion species 554, ion packet 560 includes ion species 562 and 564, and ion packet 570 includes ion species 572 and 574.

Various combinations of multiplex ion packets and single species ion packets can be used to react a single precursor species with a single reagent species, a single precursor species with multiple reagent species, multiple precursor species with a single reagent species, or multiple precursor species with multiple reagent species.

Figure 6:
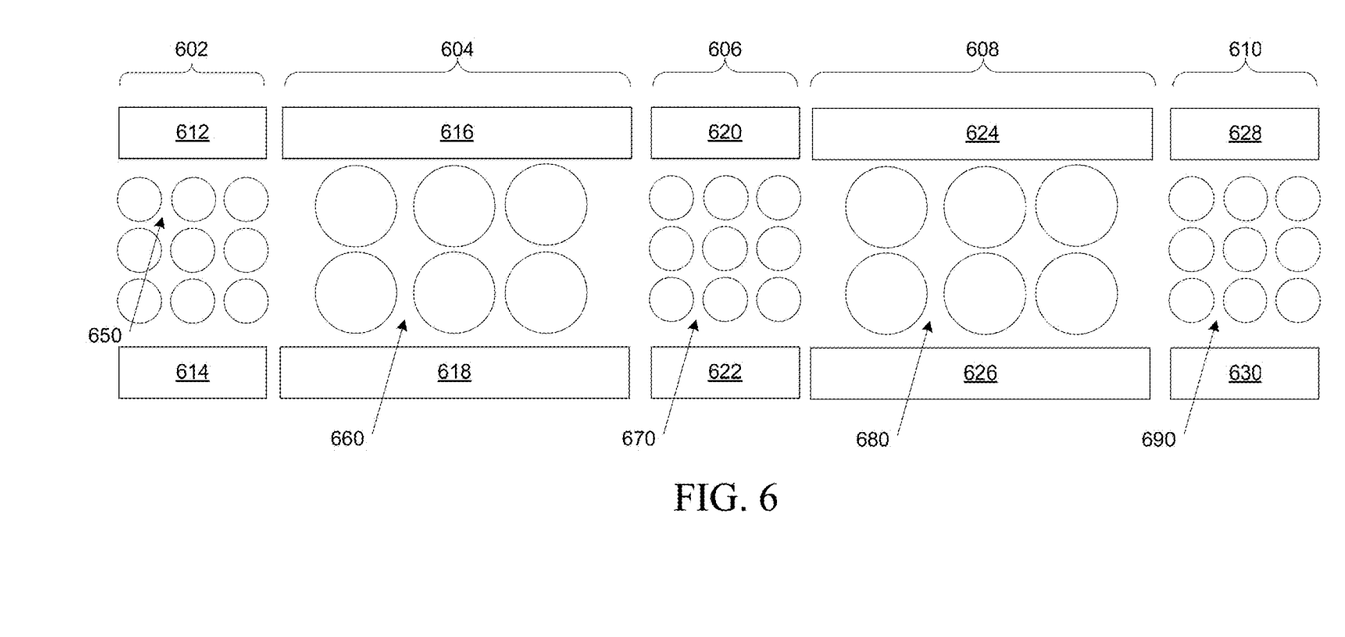

FIG. 6 illustrates a five segment segmented ion trap 600. Ion trap 600 includes segments 602, 604, 606, 608, and 610 and the segments include rods 212 and 614, rods 616 and 618, rods 620 and 622, rods 624 and 626, and rods 628 and 630 respectively. As shown, ion trap 600 is loaded with ion packet 650 in segment 602, ion packet 660 in segment 604, ion packet 670 in segment 606, ion packet 680 in segment 608, and ion packet 690 in segment 610.

Figure 7:
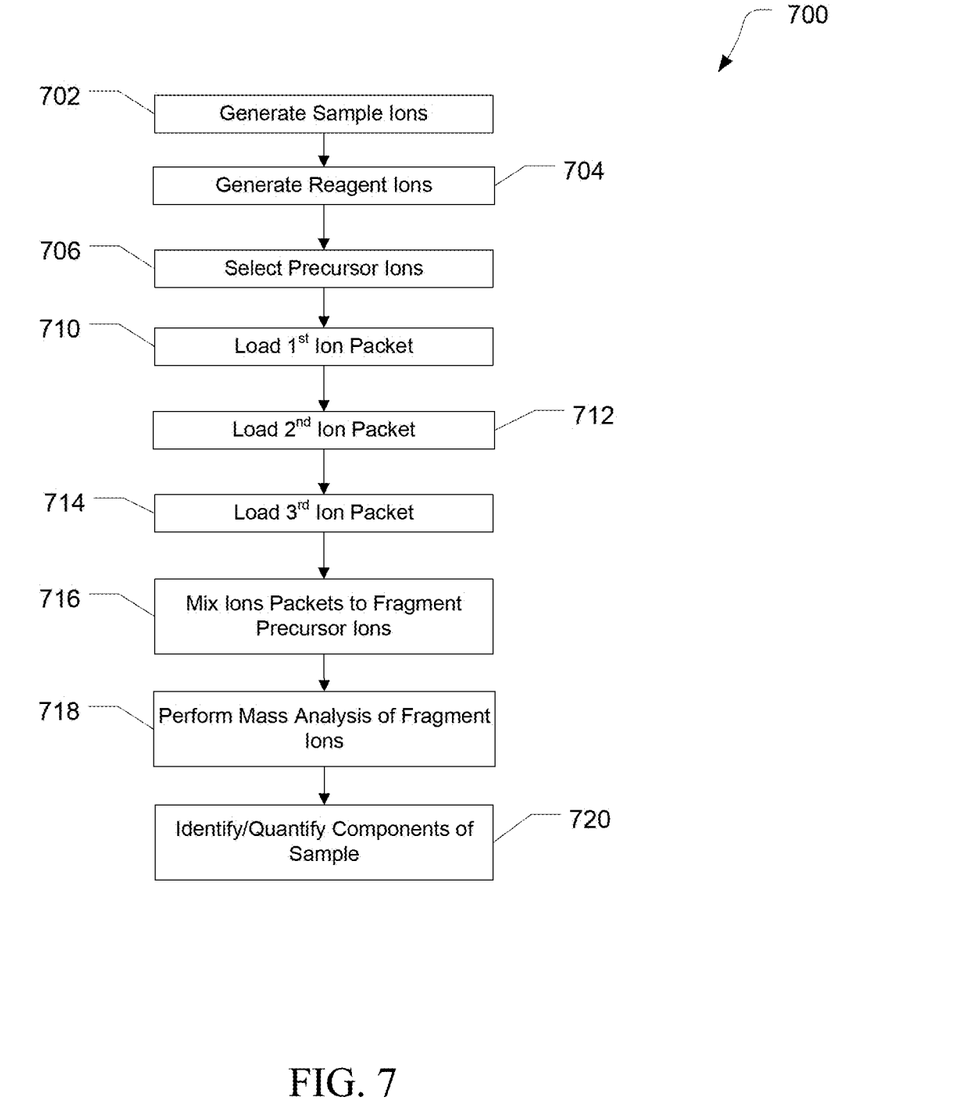
FIGS. 7, 8, and 9 are flow diagrams illustrating exemplary methods of loading a reaction cell, in accordance with various embodiments.

FIG. 7 is a flow diagram illustrating an exemplary method of reacting precursor ions with reagent ions in a reaction cell. In various embodiments, the reaction cell can include a segmented linear ion trap, a multipurpose dissociation cell, or the like. At 702, sample ions can be generated, such as in ion source 102 of system 100. In various embodiments, the sample can be supplied to an ion source such as a matrix assisted laser desorption/ionization (MALDI) source, electrospray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

At 704, reagent ions can be generated from an ion source. In various embodiments, a system can include a second ion source for the generation of the reagent ions, such as from a reagent gas or a reagent solution. Alternatively, the reagent ions can be generated in the same ion source as the sample ions, such as by alternating between supplying a sample solution and a reagent solution to the source.

At 706, precursor ions can be selected from the sample ions. In various embodiments, the sample ions may undergo some separation or selection process, such as by using a quadrupole mass filter, an ion trap, an ion mobility separator, a time-of-flight separator or the like. In various embodiments, the selection of precursor ions may select for one or more different precursor ion species, either by isolating each species individually and combining them as a single ion packet, or by substantially simultaneous selection of the different precursor ion species.

At 710, a first ion packet can be loaded into a segmented reaction cell. Various methods known in the art can be used to load the ions into the segmented reaction cell. Generally, ions are guided into the segmented reaction cell and held in a segment of the ion trap using a combination of RF and DC fields. Neutral gas molecules may be present in the segmented reaction cell for collisional cooling of the ions. In various embodiments, the ions can be moved between segments in the segmented reaction cell by manipulating the DC fields.

At 712 and 714, second and third ion packets can be loaded into the remaining segments of the ion trap. The ion packets can be substantially isolated from one another in separate segments of the ion trap using DC field gradients.

In various embodiments, the ion packets can be produced and loaded into the trap in various orders. For example, the ion packets can be handled sequentially, for example, an ion packet can be produced and loaded into the trap before the next ion packet is produced. Alternatively, the ion packets can be handled in parallel, such that ion packets can be produced concurrently or an ion packet can be produced while another ion packet is being loaded into the ion trap.

In various embodiments, one or more of the ion packets can include precursor ions and one or more of the ion packets can include reagent ions. For example, the second ion packet can include precursor ions and the first and third ion packets can include reagent ions. In various embodiments, the first and third ion packets can be different reagent ion species or the same reagent ion species. Alternatively, the first and third ion packets can include precursor ions and the second ion packet can include reagent ions. In various embodiments, the first and third ion packets can be different precursor ion species or the same precursor ion species.

In various embodiments, an ion packet can contain a single predominant species of precursor or reagent ion. Alternatively, an ion packet can be multiplexed to contain two or more significant ion species. For example, two or more precursor ion species can be co-isolated, such as by using a multi-notch isolation waveform. Alternatively, the different ion species can be isolated separately and combined to form an ion packet. For example, a first ion species can be isolated, such as by using a quadrupole mass filter or a mass selective ion trap, and then passed to an ion storage device. A second ion species can be isolated and pass to the ion storage device to form an ion packet including the first and second ion species. The ion packet can then be directed to the segmented reaction cell as a single packet. Alternatively, the first and second ion species can be isolated individually and sequentially loaded into to the same segment of the segmented reaction cell where they can be stored as a single ion packet while other ion packets are loaded into the segmented reaction cell. Similarly, different species of reagent ions can be effectively combined in a single ion packet.

In various embodiments, the first, second and third ion packets can contain different ion species or groups of ion species. For example, the first ion packet can contain a first reagent ion species, the second ion packet can contain a first and a second precursor ion species, and the third ion packet can contain a second reagent ion species. Alternatively, multiple ion packets can include the same ion species. For example, the first and third ion packets can include a reagent ion species, and the second ion packet can include a precursor species.

In various embodiments, the segmented reaction cell can include additional segments, such as a total of four or more segments, and the additional segments can be loaded with additional ion packets containing either precursor ions or reagent ions.

At 716, the ion packets can be mixed to allow the precursor and reagent ions to react. In various embodiments, the reagent ions and the precursor ions can be mixed within the segmented reaction cell and the reagent ions can react with the precursor ions to form product ions, such as to cause fragmentation of the precursor ions or to enable a proton transfer reaction. In various embodiments, reagent ions and precursor ions can be mixed by applying an RF pseudo-potential to end lenses of the reaction cell. The RF pseudo-potential can be effective to prevent both anions and cations from exiting the reaction cell axially. With the RF pseudo-potential in place to trap the ions, the DC fields containing the ion packets within the respective segments can be removed, allowing the ions to mix. In particular embodiments, the RF pseudo-potential can force both the cations and the anions towards the center of the trap, increasing the ion density and the likelihood of ion-ion interactions.

In various embodiments, a single ion packet would contain either precursor ions or reagent ions but not both so as to isolate the precursor ions from the reagent ions such that the timing, duration, and conditions of the reactions can be controlled.

At 718, mass analysis can be performed on the fragment ions. In various embodiments, the reaction cell can be used to conduct the mass analysis. In other embodiments, the product ions can be extracted from the reaction cell for mass analysis. In various embodiments, the product ions can be scanned out of the reaction cell to an ion detector such that the mass-to-charge ratios of the ions can be determined based on conditions under which they are ejected from the ion trap. Alternatively, all or a subset of the ions can be driven from the reaction cell into an electrostatic trap mass analyzer or a time-of-flight mass analyzer and the mass-to-charge ratios of the product ions can be determined substantially independent of the conditions under which they leave the reaction cell.

At 720, components of the sample can be identified based on the mass-to-charge ratio of the product ions and optionally the mass-to-charge ratio of the precursor ions. Additionally, the components may be quantified based on the intensity of the precursor or product ions.

Figure 8:
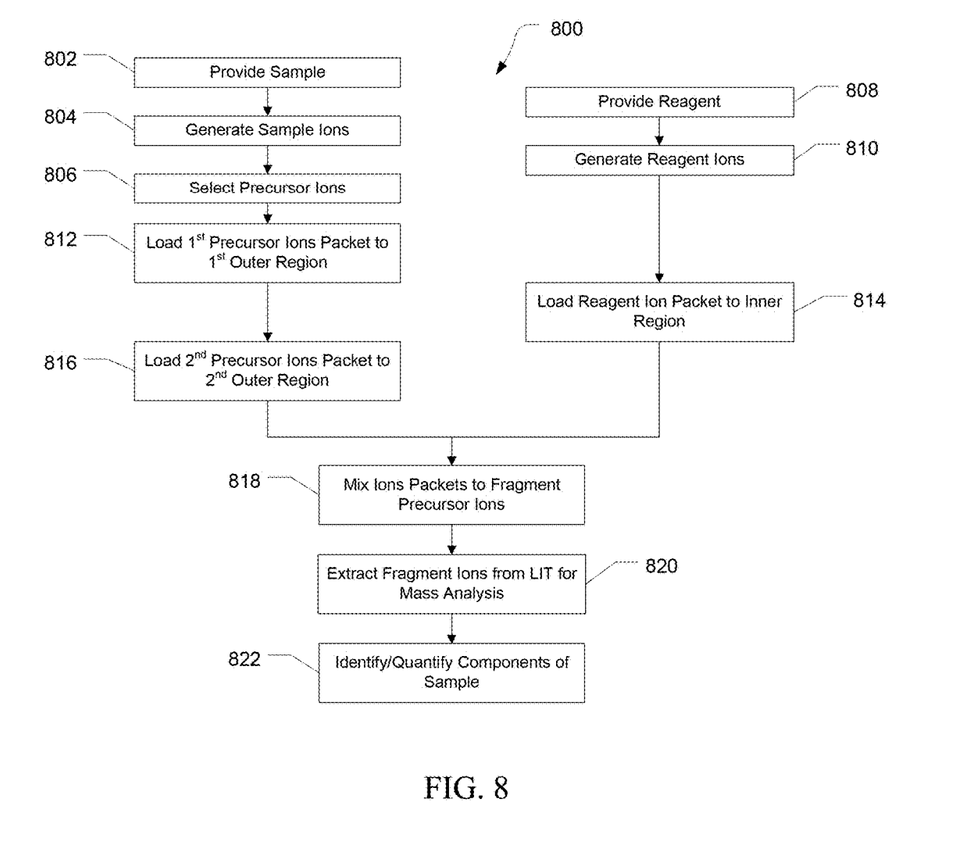

FIG. 8 is a flow diagram illustrating an exemplary method of reacting precursor ions with reagent ions in a reaction cell. At 802, a sample can be provided to a sample ion source such as ion source 102 of system 100, and at 804, sample ions can be generated. At 806, precursor ions can be selected from the sample ions.

At 808, a reagent can be provided to an ion source and at 810 reagent ions can be generated. In various embodiments, a system can include a second ion source for the generation of the reagent ions, such as from a reagent gas or a reagent solution. Alternatively, the reagent ions can be generated in the same ion source as the sample ions, such as by alternating between supplying a sample solution and a reagent solution to the source.

At 812, a first precursor ion packet can be loaded into a first outer segment of a segmented reaction cell. At 814, a reagent ion packet can be loaded into an inner segment of a segmented reaction cell. At 816, a second precursor ion packet can be loaded into a second outer segment of a segmented reaction cell.

At 818, the ion packets can be mixed to react the precursor and reagent ions to form product ions, such as by fragmenting the precursor ions. At 820, mass analysis can be performed on the fragment ions. At 822, components of the sample can be identified based on the mass-to-charge ratio of the product ions and optionally the precursor ions thereof. Additionally, the components may be quantified based on the intensity of the precursor or product ions.

Figure 9:
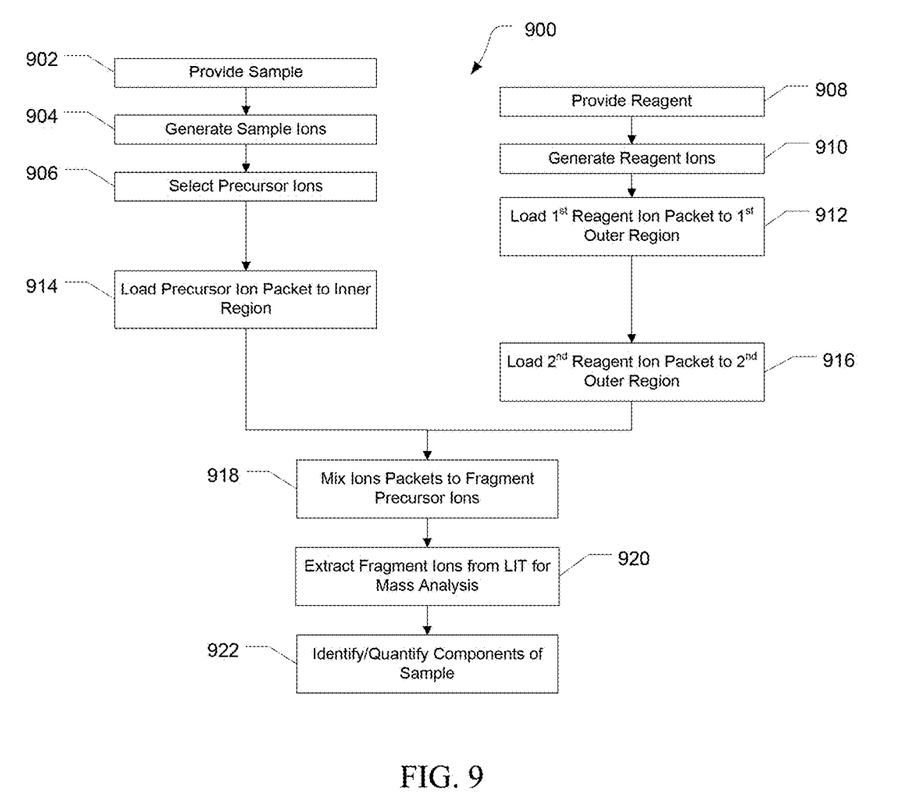

FIG. 9 is a flow diagram illustrating an exemplary method of reacting precursor ions with reagent ions in a reaction cell. At 902, a sample can be provided to a sample ion source such as ion source 102 of system 100, and at 904, sample ions can be generated. At 906, precursor ions can be selected from the sample ions.

At 908, a reagent can be provided to an ion source and at 910 reagent ions can be generated. In various embodiments, a system can include a second ion source for the generation of the reagent ions, such as from a reagent gas or a reagent solution. Alternatively, the reagent ions can be generated in the same ion source as the sample ions, such as by alternating between supplying a sample solution and a reagent solution to the source.

At 912, a first reagent ion packet can be loaded into a first outer segment of a segmented reaction cell. At 914, a precursor ion packet can be loaded into an inner segment of a segmented reaction cell. At 916, a second reagent ion packet can be loaded into a second outer segment of a segmented reaction cell.

At 918, the ion packets can be mixed to allow the precursor ions and the reagent ions to react to form product ions, such as by fragmenting the precursor ions. At 920, mass analysis can be performed on the fragment ions. At 922, components of the sample can be identified based on the mass-to-charge ratio of the product ions and optionally the precursor ions. Additionally, the components may be quantified based on the intensity of the precursor or product ions.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A method for analyzing a sample, comprising:
   trapping a first ion packet in a first segment of a multi-segment reaction cell;
   trapping a second ion packet in a second segment of the multi-segment reaction cell;
   trapping a third ion packet in a third segment of the multi-segment reaction cell, wherein at least one of the first, second, and third ion packets includes precursor ions, and at least another one of the first, second, and third ion packets includes reagent ions; and
   mixing the first, second, and third ion packets within the reaction cell to cause a reaction between the precursor ions and the reagent ions to form product ions,
   wherein the precursor ions include a mixture of more than one precursor ion species.

2. The method of claim 1 further comprising supplying a sample to an ion source and generating the precursor ions.

3. The method of claim 1 further comprising supplying a reagent to an ion source and generating the reagent ions.

4. The method of claim 1 further comprising directing the product ions to a mass analyzer to determine the mass-to-charge ratio of the product ions.

5. The method of claim 4 further comprising identifying a component of the sample based on the mass-to-charge ratio of the product ions.

6. The method of claim 1 wherein the first and third segments are outer segments of the multi-segment reaction cell and the second segment is a center segment of the multi-segment reaction cell.

7. The method of claim 1 wherein the first and third ion packets include reagent ions and the second ion packet includes precursor ions.

8. The method of claim 1 wherein the first and third ion packets include precursor ions and the second ion packet includes reagent ions.

9. The method of claim 1 wherein the more than one precursor ion species are in separate ion packets.

10. The method of claim 1 wherein the more than one precursor ion species are in the same ion packet.

11. A method for analyzing a sample, comprising:
    trapping a first ion packet in a first segment of a multi-segment reaction cell;
    trapping a second ion packet in a second segment of the multi-segment reaction cell;
    trapping a third ion packet in a third segment of the multi-segment reaction cell, wherein at least one of the first, second, and third ion packets includes precursor ions, and at least another one of the first, second, and third ion packets includes reagent ions; and
    mixing the first, second, and third ion packets within the reaction cell to cause a reaction between the precursor ions and the reagent ions to form product ions,
    wherein the reagent ions include a mixture of more than one reagent ion species.

12. The method of claim 11 wherein the more than one reagent ion species are in separate ion packets.

13. The method of claim 11 wherein the more than one reagent ion species are in the same ion packet.

14. The method of claim 1 further comprising trapping additional ion packets in additional segments of the multi-segment reaction cell prior to mixing the ion packets.

15. A system for analyzing a sample comprising:
    a multi-segment reaction cell including at least first, second, and third segments;
    a sample ion source configured to receive a sample and generate precursor ions;
    a mass analyzer configured to determine the mass-to-charge ratio of product ions;

a controller configured to:
  instruct the trapping of a first ion packet in a first segment of the multi-segment reaction cell;
  instruct the trapping of a second ion packet in a second segment of the multi-segment reaction cell;
  instruct the trapping of a third ion packet in a third segment of the multi-segment reaction cell, wherein at least one of the first, second, and third ion packets includes precursor ions, and at least another one of the first, second, and third ion packets includes reagent ions; and
  instruct the mixing of the first, second, and third ion packets within the reaction cell to cause a reaction between the precursor ions and the reagent ions to form product ions,
  wherein the precursor ions include a mixture of more than one precursor ion species.

16. The system of claim 15 further comprising a reagent ion source configured to receive a reagent and generate reagent ions.

17. The system of claim 15 wherein the sample ion source is further configured to receive a reagent and generate reagent ions.

18. The system of claim 15 further comprising a processor configured to identifying a component of the sample based on the mass-to-charge ratio of the product ions.

19. The system of claim 15 wherein the first and third ion packets include reagent ions and the second ion packet includes precursor ions.

20. The system of claim 15 wherein the first and third ion packets include precursor ions and the second ion packet includes reagent ions.

21. A system for analyzing a sample comprising:
a multi-segment reaction cell including at least first, second, and third segments;
a sample ion source configured to receive a sample and generate precursor ions;
a mass analyzer configured to determine the mass-to-charge ratio of product ions;
a controller configured to:
  instruct the trapping of a first ion packet in a first segment of the multi-segment reaction cell;
  instruct the trapping of a second ion packet in a second segment of the multi-segment reaction cell;
  instruct the trapping of a third ion packet in a third segment of the multi-segment reaction cell, wherein at least one of the first, second, and third ion packets includes precursor ions, and at least another one of the first, second, and third ion packets includes reagent ions; and
  instruct the mixing of the first, second, and third ion packets within the reaction cell to cause a reaction between the precursor ions and the reagent ions to form product ions,
  wherein the reagent ions include a mixture of more than one reagent ion species.

22. The system of claim 15 wherein the multi-segment reaction cell includes additional segments and the controller is further configured to instruct the trapping of additional ion packets in the additional segments of the multi-segment reaction cell prior to mixing the ion packets.

23. The system of claim 15 wherein the multi-segment reaction cell is a segmented linear ion trap, a higher-energy dissociation (HCD) cell, a multipurpose dissociation cell, or any combination thereof.

* * * * *